United States Patent
He et al.

(10) Patent No.: US 6,849,116 B2
(45) Date of Patent: Feb. 1, 2005

(54) QUINOPHTHALONE-DERIVATIVE BASED CRYSTALLIZATION MODIFIERS

(75) Inventors: Jianing He, Ludwigshafen (DE); Manfred Schröck, Birkenheide (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/311,320

(22) PCT Filed: Jun. 22, 2001

(86) PCT No.: PCT/EP01/07128
§ 371 (c)(1),
(2), (4) Date: Dec. 30, 2002

(87) PCT Pub. No.: WO02/00643
PCT Pub. Date: Jan. 3, 2002

(65) Prior Publication Data
US 2003/0172847 A1 Sep. 18, 2003

(30) Foreign Application Priority Data
Jun. 29, 2000 (DE) .......................... 100 30 780

(51) Int. Cl.$^7$ ...................... C07D 401/04; C09B 25/00; C09D 11/00
(52) U.S. Cl. ................. 106/498; 106/31.76; 106/413; 106/493; 106/494; 106/495; 106/496; 106/497; 8/657; 347/100; 430/7; 430/108.2; 524/83; 524/86; 524/87; 524/95; 544/363; 546/154; 546/171; 546/173
(58) Field of Search .................. 106/31.76, 413, 106/493, 494, 495, 496, 497, 498; 8/657; 347/100; 430/7, 108.2; 524/83, 86, 87, 95; 544/363; 546/154, 171, 173

(56) References Cited

U.S. PATENT DOCUMENTS

| | | | | |
|---|---|---|---|---|
| 4,067,870 A | * | 1/1978 | Shimada et al. | ............ 546/167 |
| 4,077,960 A | * | 3/1978 | Shimada et al. | ............... 546/99 |
| 4,150,025 A | * | 4/1979 | Shimada et al. | ............... 546/99 |

FOREIGN PATENT DOCUMENTS

| | | | |
|---|---|---|---|
| DE | 17 70 960 | | 1/1972 |
| DE | 26 26 271 | | 12/1976 |
| DE | 26 38 528 | | 3/1977 |
| DE | 27 06 872 | | 8/1977 |
| EP | 0 335 237 | | 10/1989 |
| EP | 001138723 A1 | * | 10/2001 |
| GB | 1486022 | * | 9/1977 |
| GB | 2008142 | * | 10/1977 |
| JP | 53-50231 A | * | 5/1978 |
| JP | 53-52537 A | * | 5/1978 |
| WO | 97 46623 | | 12/1997 |
| WO | 98 32802 | | 7/1998 |
| WO | 01 27206 | | 4/2001 |

OTHER PUBLICATIONS

Chemical Abstract No. 90:105638, abstract of Japanese Patent Specification No. 53–121822 (Oct. 1978).*

* cited by examiner

*Primary Examiner*—Anthony J. Green
(74) *Attorney, Agent, or Firm*—Oblon, Spivak, McClelland, Maier & Neustadt, P.C.

(57) ABSTRACT

Quinophthalone derivatives have the general formula I where
$R^1$, $R^2$, $R^3$ and $R^5$ are independently hydrogen, halogen or $C_1$–$C_4$-alkyl;
$R^4$ is —$SO_3H$, —$SO_3^-N^+R^6R^7R^8R^9$, —$SO_2NR^6R^7$, —$CH_2NR^6R^7$, —$CH_2R^{10}$, —COOH, —COO$^-$N$^+$ $R^6R^7R^8R^9$, —COOR$^{11}$, —COR$^{11}$, —$NO_2$ or $C_1$–$C_4$-alkyl;
$R^6$, $R^7$, $R^8$ and $R^9$ are independently hydrogen; $C_1$–$C_{22}$-alkyl or $C_2$–$C_{22}$-alkenyl whose carbon chains may be interrupted by one or more moieties selected from the group consisting of —O—, —S—, —NR$^{12}$—, —CO— and —$SO_2$— and/or which may each be mono- or polysubstituted by hydroxyl, halogen, aryl, $C_1$–$C_4$-alkoxy and/or acetyl; $C_3$–$C_8$-cycloalkyl whose carbon skeleton may be interrupted by one or more moieties selected from the group consisting of —O—, —S—, —NR$^{12}$— and —CO— and/or which may be mono- or polysubstituted by hydroxyl, halogen, aryl, $C_1$–$C_4$-alkoxy and/or acetyl; dehydroabietyl or aryl; $R^6$ and $R^7$ or $R^6$, $R^7$ and $R^8$ are together a 5- to 7-membered cyclic radical which includes the nitrogen atom and may include further heteroatoms; $R^{10}$ is $R^{11}$ is alkyl $R^6$;
$R^{12}$ is hydrogen or $C_1$–$C_4$-alkyl;
$X^1$, $X^2$ and $X^3$: are independently arylene, which may be substituted by halogen, arylsulfonyl or —COR$^{13}$ or —CO—$C_6H_4$—CO—;
$R^{13}$ is $C_1$–$C_3$-alkyl or phenyl.

18 Claims, No Drawings

QUINOPHTHALONE-DERIVATIVE BASED CRYSTALLIZATION MODIFIERS

The present invention relates to quinophthalone derivatives of the general formula I

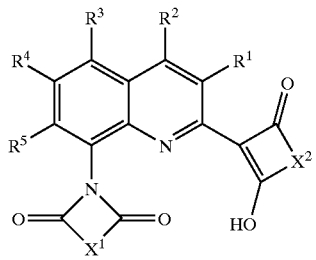

where

R$^1$, R$^2$, R$^3$ and R$^5$ are independently hydrogen, halogen or C$_1$–C$_4$-alkyl;

R$^4$ is —SO$_3$H, —SO$_3^-$N$^+$R$^6$R$^7$R$^8$R$^9$, —SO$_2$NR$^6$R$^7$, —CH$_2$NR$^6$R$^7$, —CH$_2$R$^1$, —COOH, —COO$^-$N$^+$R$^6$R$^7$R$^8$R$^9$, —COOR$^{11}$, —COR$^{11}$, —NO$_2$ or C$_1$–C$_4$-alkyl;

R$^6$, R$^7$, R$^8$ and R$^9$ are independently hydrogen; C$_1$–C$_{22}$-alkyl or C$_2$–C$_{22}$-alkenyl whose carbon chains may be interrupted by one or more moieties selected from the group consisting of —O—, —S—, —NR$^{12}$—, —CO— and —SO$_2$— and/or which may each be mono- or polysubstituted by hydroxyl, halogen, aryl, C$_1$–C$_4$-alkoxy and/or acetyl; C$_3$–C$_8$-cycloalkyl whose carbon skeleton may be interrupted by one or more moieties selected from the group consisting of —O—, —S—, —NR$^{12}$— and —CO— and/or which may be mono- or polysubstituted by hydroxyl, halogen, aryl, C$_1$–C$_4$-alkoxy and/or acetyl; dehydroabietyl or aryl; R$^6$ and R$^7$ or R$^6$, R$^7$ and R$^8$ are together a 5- to 7-membered cyclic radical which includes the nitrogen atom and may include further heteroatoms;

R$^{10}$ is

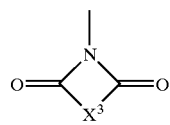

R$^{11}$ is alkyl R$^6$;
R$^{12}$ is hydrogen or C$_1$–C$_4$-alkyl;
X$^1$, X$^2$ and X$^3$ are independently arylene, which may be substituted by halogen, arylsulfonyl or —COR$^{13}$ or —CO—C$_6$H$_4$—CO—;
R$^{13}$ is C$_1$–C$_3$-alkyl or phenyl, and to their use as crystallization modifiers for organic pigments.

The invention further provides a process for transforming crude quinophthalone pigments into a finely divided pigmentary state.

The invention finally relates to quinophthalone pigments of the general formula II

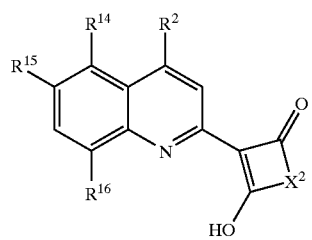

where
R$^2$ is hydrogen, halogen or C$_1$–C$_4$-alkyl;
one of R$^{14}$, R$^{15}$ and R$^{16}$ is

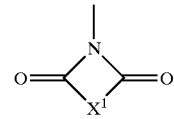

and the others are each hydrogen;
X$^1$ and X$^2$ are independently arylene, which may be substituted by halogen, arylsulfonyl or —COR$^{13}$ or —CO—C$_6$H$_4$—CO—;
R$^{12}$ is C$_1$–C$_3$-alkyl or phenyl,
characterized by an isometric particle shape and a particle size of from 50 to 200 nm coupled with a width of ±20 nm for the particle size distribution, and also to pigment preparations including
A) at least one quinophthalone pigment II and
B) at least one quinophthalone derivative I,
and their use for coloring plastics, paints, printing inks, inkjet inks, color filters and electrophotographic toners.

Quinophthalone pigments have a stability, especially with regard to light, weathering and heat, that makes them useful yellow pigments. A particularly important representative of this class of pigment is C.I. Pigment Yellow 138 (cf. DE-A-17 70 960). Further quinophthalone pigments are described in DE-A-26 26 271, 26 38 528 and 27 06 872.

As-synthesized quinophthalone pigments are coarsely crystalline and have a highly heterogeneous particle size distribution. These crude pigments are therefore usually subjected to a finishing treatment to transform them into a pigmentary state useful for color applications.

DE-A-23 57 077 discloses a finishing treatment comprising grinding the crude pigment and subsequently recrystallizing the millbase in an organic solvent. DE-A-27 46 164 discloses wet grinding in aqueous suspension in high speed stirred ball mills.

It is true that the methods described do provide particle comminution and hence an improvement in the color property of the pigments, albeit very time-consumingly in some instances and with no control over the particle size of the pigments obtained, which generally have an inadequate, because excessively broad, particle size distribution for a whole series of applications, for example as colorants in inkjet inks, color filters and electrophotographic toners.

It is an object of the present invention to remedy these disadvantages and provide quinophthalone pigments having advantageous application properties, including in particular advantageous particle size distributions.

We have found that this object is achieved by the quinophthalone derivatives of the formula I defined at the beginning and their use as crystallization modifiers for organic pigments.

Preferred quinophthalone derivatives I are revealed in the subclaim.

The invention also provides a process for transforming crude quinophthalone pigments into a finely divided pigmentary state, which comprises finishing the crude quinophthalone pigment in the presence of one or more quinophthalone derivatives of the formula I.

Finally, the invention provides the quinophthalone pigments of the above-defined formula II that are characterized by an isometric particle shape and a particle size of 50 to 200 nm coupled with a width of ±20 nm for the particle size distribution, and also pigment preparations including
A) at least one quinophthalone pigment II and B) at least one quinophthalone derivative I
and their use for coloring plastics, paints, printing inks, inkjet inks, color filters and electrophotographic toners.

Any alkyl and alkenyl appearing in the formula I and the hereinbelow described formulae I, II and III may be straight-chain or branched.

Specific examples of alkyl are methyl, ethyl, propyl, isopropyl, butyl, isobutyl, sec-butyl, tert-butyl, pentyl, isopentyl, neopentyl, tert-pentyl, hexyl, 2-methylpentyl, heptyl, 1-ethylpentyl, octyl, 2-ethylhexyl, isooctyl, nonyl, isononyl, decyl, isodecyl, undecyl, dodecyl, tridecyl, isotridecyl, tetradecyl, pentadecyl, hexadecyl, heptadecyl, octadecyl, nonadecyl and eicosyl (the above designations isooctyl, isononyl, isodecyl and isotridecyl are trivial names derived from the alcohols obtained by the oxo process).

Examples of alkyl radicals whose carbon chains may be interrupted by one or more moieties selected from the group consisting of —O—, —S—, —NR$^{12}$—, —CO— and —SO$_2$— and of alkoxy- and alkanoyl-substituted alkyl radicals are:

2-methoxyethyl, 2-ethoxyethyl, 2-propoxyethyl, 2-isopropoxyethyl, 2-butoxyethyl, 2- and 3-methoxypropyl, 2- and 3-ethoxypropyl, 2- and 3-propoxypropyl, 2- and 3-butoxypropyl, 2- and 4-methoxybutyl, 2- and 4-ethoxybutyl, 2- and 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9-trioxaundecyl, 3,6,9-trioxadodecyl, 3,6,9,12-tetraoxatridecyl and 3,6,9,12-tetraoxatetradecyl;

2-methylthioethyl, 2-ethylthioethyl, 2-propylthioethyl, 2-isopropylthioethyl, 2-butylthioethyl, 2- and 3-methylthiopropyl, 2- and 3-ethylthiopropyl, 2- and 3-propylthiopropyl, 2- and 3-butylthiopropyl, 2- and 4-methylthiobutyl, 2- and 4-ethylthiobutyl, 2- and 4-propylthiobutyl, 3,6-dithiaheptyl, 3,6-dithiaoctyl, 4,8-dithianonyl, 3,7-dithiaoctyl, 3,7-dithianonyl, 4,7-dithiaoctyl, 4,7-dithianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiatridecyl and 3,6,9,12-tetrathiatetradecyl;

2-monomethyl- and 2-monoethylaminoethyl, 2-dimethylaminoethyl, 2- and 3-dimethylaminopropyl, 3-monoisopropylaminopropyl, 2- and 4-monopropylaminobutyl, 2- and 4-dimethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazaundecyl, 12-methyl-3,6,9,12-tetraazatridecyl and 3,6,9,12-tetramethyl-3,6,9,12-tetraazatridecyl;

propan-2-on-1-yl, butan-3-on-1-yl, butan-3-on-2-yl and 2-ethylpentan-3-on-1-yl;

2-methylsulfonylethyl, 2-ethylsulfonylethyl, 2-propylsulfonylethyl, 2-isopropylsulfonylethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylpropyl, 2- and 4-methylsulfonylbutyl, 2- and 4-ethylsulfonylbutyl, 2- and 4-propylsulfonylbutyl and 4-butylsulfonylbutyl.

Examples of C$_2$–C$_{22}$-alkenyl radicals are oleyl, linoleyl and linolenyl.

Examples of alkoxy are methoxy, ethoxy, propoxy, isopropoxy, butoxy, isobutoxy, sec-butoxy and tert-butoxy.

Examples of cycloalkyl are cyclopropyl, cyclobutyl, cyclopentyl, cyclohexyl, cycloheptyl and cyclooctyl. Cycloalkyl radicals containing heteroatoms include for example dioxanyl, morpholinyl, tetrahydrofuryl, pyrrolidinyl and piperidinyl.

Examples of aryl are phenyl and 1- and 2-naphthyl.

Halogen is in particular chlorine or bromine, preferably chlorine.

Substituted alkyl radicals preferably have a chain of up to 6 carbon atoms and preferably bear one or two substituents. Examples are 2-hydroxyethyl, 2- and 3-hydroxypropyl, 1-hydroxyprop-2-yl and 2- and 4-hydroxybutyl and benzyl.

Examples of 5- to 7-membered cyclic radicals containing the nitrogen atom and formed from R$^6$ and R$^7$ or R$^6$ to R$^8$, which may be benzofused, are morpholinyl, pyrrolidinyl, piperidyl, pyrryl, pyridyl, pyrimidyl, pyrazolyl, imidazolyl, thiazolyl, triazyl, quinaldyl, quinolinyl, benzoxazolyl, benzothiazolyl, benzothiadiazolyl, benzimidazolyl and isoquinolyl.

Examples of arylene and substituted arylene X$^1$ to X$^3$ are 1,2-phenylene, tetrachloro- and tetrabromo-1,2-phenylene, 1,2-naphthylene, 2,3-naphthylene, 1,8-naphthylene and 2,2'-biphenylene, of which 1,2-phenylene and tetrachloro-1,2-phenylene are preferred.

Examples of acyl are acetyl, propionyl, butyryl and benzyl.

Examples of useful alkoxycarbonyl radicals are methoxycarbonyl, ethoxycarbonyl, propoxycarbonyl, butoxycarbonyl, pentoxycarbonyl and hexoxycarbonyl.

Examples of acyl radicals are methylcarbonyl, ethylcarbonyl, propylcarbonyl, butylcarbonyl and pentylcarbonyl.

Examples of arylsulfonyl radicals are in particular phenylsulfonyl and substituted phenylsulfonyl such as p-tolylsulfonyl, p-chlorophenylsulfonyl and p-bromophenylsulfonyl.

The quinophthalone derivatives I are advantageously prepared from the quinophthalones of the general formula III

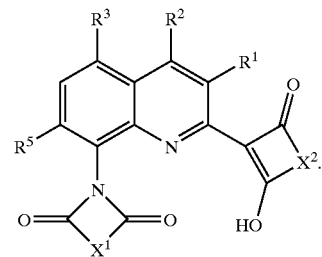

III

Reacting the quinophthalones III with oleum is a way to obtain the quinophthalone derivatives of the formula I where R$^4$ is —SO$_3$H.

This sulfonation is advantageously carried out using an oleum having a sulfur trioxide content of from 0.1 to 65% by weight, especially from 5 to 25% by weight.

The amount of oleum is not critical per se. Since the oleum also acts as solvent, the amount of oleum used should at least be sufficient for the solution to remain stirrable. The amount of oleum used per g of quinophthalone III is customarily in the range from 1 to 10 g, preferably about 3–7 g.

The reaction temperature is generally in the range from 0 to 200° C., preferably in the range from 50 to 100° C.

The reaction time may be in the range from 1 to 20 h. Generally, the regioselective sulfonation will have ended in the course of about 6 h.

The product is typically collected by filtration after the reaction mixture has been hydrolyzed in ice-water.

Further reaction with amines or quaternary ammonium salts can be used to convert the sulfonated quinophthalone derivatives I into the corresponding ammonium salts I ($R^4$: —$SO_3^- N^+ R^6 R^7 R^8 R^9$), which are stronger inhibitors of crystal growth than the sulfonated quinophthalone derivatives I and also promote the formation of a particularly readily dispersible pigment.

Useful amines include primary, secondary and tertiary amines. Secondary and tertiary amines may each contain identical or different alkyl groups. It is also possible to use for example fatty amines having linear, hydrogenated or unsaturated alkyl radicals. Especially shorter alkyl radicals having up to 6 carbon atoms may also be branched and/or bear up to two substituents preferably selected from the group consisting of hydroxyl, acetyl, methoxy, ethoxy, chlorine and bromine.

Examples of particularly preferred amines and ammonium salts are stearylamine, methyldistearylamine, dimethylstearylamine and dehydroabietylamine and dimethyldistearylammonium salts.

Ammonium salt formation may also be effected in organic solvents, water or aqueous-organic media in a generally customary manner. Suitable reaction temperatures generally range from 20 to 100° C. The product may likewise be collected by filtration.

However, the ammonium salt may also be formed in the course of the pigment finishing process of the invention, which comprises a grinding step and a recrystallization step, by adding approximately equimolar amounts of the sulfoquinophthalone derivative I and of the amine or ammonium salt in the course of one of the two finishing steps.

Quinophthalone derivatives of the formula I where $R^4$ is —$SO_2 NR^6 R^7$ may advantageously be prepared by sulfochlorination and subsequent amidation.

The quinophthalone III is customarily sulfochlorinated using chlorosulfonic acid. Advantageously the product obtained is additionally reacted with thionyl chloride to ensure that all sulfonic acid groups have been converted into the acyl chloride.

The amount of chlorosulfonic acid is likewise not critical per se. However, to obtain stirrable solutions it is customary to use from 1 to 10 g, preferably about 4 g, of chlorosulfonic acid per g of quinophthalone III.

This reaction is generally carried out at from 80 to 180° C., preferably at from 100 to 130° C., and takes about 1–20 h, preferably about 2 h.

When the product is subsequently reacted with thionyl chloride, the reaction mixture obtained is advantageously cooled down to about 70–80° C. and then generally from 0.3 to 1 g, especially from 0.4 to 0.7 g, of thionyl chloride are added per g of quinophthalone III.

After a further reaction time of generally from 0.5 to 2 h, the regioselectively monosulfochlorinated product can be collected by filtration after hydrolysis in ice-water. The product is then customarily amidated without prior drying. The amidation is carried out using a primary or a secondary amine. The reaction is preferably carried out using the above-recited amines.

The amidation is preferably effected in an approximately neutral aqueous medium. To maintain a pH of about 7 it is advisable to employ a buffer, for example sodium acetate.

The amidation is customarily effected at from 0 to 20° C. and takes about 0.5 to 5 h, especially 1–2 h.

The quinophthalone derivatives of the formula I where $R^4$ is —$CH_2 NR^6 R^7$ or —$CH_2 R^{10}$ may be obtained by methylamidating the quinophthalones III in a Tscherniac-Einhorn reaction.

The preferred phthalimidomethylquinophthalones I may thus be prepared by reaction with paraformaldehyde and phthalimide in concentrated sulfuric acid, which may include from 0.1 to 10% by weight, preferably 3% by weight, of sulfur trioxide (from 0.1 to 10% by weight, preferably 3% by weight, oleum).

The amounts used per g of quinophthalone III are generally from 0.05 to 0.2 g, preferably from 0.06 to 0.1 g, of paraformaldehyde and from 0.1 to 0.3 g, preferably from 0.2 to 0.25 g, of phthalimide.

The amount of sulfuric acid or oleum is not critical per se. The amount used per g of quinophthalone III is generally from 1 to 10 g, especially about 5 g.

In an advantageous process for carrying out this reaction, sulfuric acid or oleum is initially charged, phthalimide and paraformaldehyde are added alternatingly and after a reaction time of from about 0.5 to 2 h at 40–60° C. the quinophthalone III is added and the mixture is allowed to react at from 80 to 120° C. for about 2–5 h.

The product is customarily collected by filtration after hydrolysis of the reaction mixture in water.

The quinophthalone derivatives of the formula I where $R^4$ is —$COR^{11}$ or —$C_1$–$C_4$-alkyl may be obtained by customary Friedel-Crafts acylation or Friedel-Crafts alkylation of the quinophthalone III. Quinophthalone derivatives of the formula I where $R^4$ is —COOH or —$COOR^{11}$ are obtainable by Friedel-Crafts acylation of III and subsequent reaction with water or alcohols. The quinophthalone derivatives I bearing nitro $R^4$ are finally obtainable by nitration of the quinophthalones III.

The quinophthalone derivatives I are very useful as crystallization modifiers for organic pigments. They make it possible for the crude pigment to be transformed into a useful, finely divided pigmentary state having a narrow particle size distribution.

They are particularly important as crystallization modifiers for quinophthalone pigments, preferably quinophthalone pigments of the above-defined formula II, particularly preferably for quinophthalone derivatives of the formula II where $R^2$, $R^{14}$ and $R^{15}$ are each hydrogen, and most preferably for C.I. Pigment Yellow 138.

In the inventive process for transforming crude quinophthalone pigments into a finely divided pigmentary state, the crude pigment is finished in the presence of one or more quinophthalone derivatives I.

In a preferred version of the process according to the invention, the as-synthesized crude pigment is ground, preferably in the absence of grinding assistants, and the millbase obtained is subsequently recrystallized in an organic solvent or a mixture of organic solvent and water in the presence of the quinophthalone derivative I.

In a second preferred version, the quinophthalone derivative I is already present during the grinding and the millbase obtained is subsequently recrystallized in an organic solvent or a mixture of organic solvent and water.

It will be appreciated that the quinophthalone derivative I may also be added in subdivided portions at different stages of the finishing process.

Finally, the grinding may also be effected directly in the presence of a recrystallizing solvent, for example $C_2$–$C_4$-alkanols, glycols, glycol ethers and dialkyl phthalates, especially diethyl phthalate and particularly dimethyl phthalate. In this case, there is no need for a subsequent recrystallization step.

The quinophthalone derivative I is generally used in an amount of from 0.1 to 10% by weight, preferably from 2 to 5% by weight, based on the crude pigment.

The grinding can be carried out in a ball mill, a vibratory mill, a planetary mill or a stirred media mill. Useful grinding media include for example iron balls, silicon/aluminum/ zirconium oxide beads, glass beads, agate balls and sand grains, which may have diameters in the range from 0.1 to 5 cm.

Grinding is preferably carried on until the millbase has a median primary particle size <30 nm. Accordingly grinding typically takes from 10 to 60 h, especially from 30 to 50 h.

The subsequent recrystallization can be carried out with a multiplicity of organic solvents.

Useful solvents are alcohols especially having up to 10 carbon atoms, ether alcohols, ethers, ketones, carboxylic acids especially having up to 4 carbon atoms, carboxamides, carboxylic esters and also alicyclic and aromatic hydrocarbons. It will be appreciated that mixtures of these solvents may also be used. Specific examples are:

methanol, ethanol, propanol, isopropanol, butanol, isobutanol, tert-butanol, amyl alcohol, isoamyl alcohol, hexanol, isohexanol, heptanol, octanol, 2-ethylhexanol, ethylene glycol, 1,2- and 1,3-propylene glycol, cyclohexanol, methylcyclohexanol, benzyl alcohol and 2-phenylethanol;

ethylene glycol monomethyl, monoethyl and monobutyl ether and diethylene glycol monomethyl and monoethyl ether;

dipropyl ether, diisopropyl ether, dibutyl ether, diisobutyl ether, tetrahydrofuran, dioxane, diethylene glycol dimethyl and diethyl ether;

acetone, methyl ethyl ketone, methyl propyl ketone, methyl butyl ketone, diethyl ketone, methyl isopropyl ketone, methyl isobutyl ketone, cyclopentanone, cyclohexanone, methylcyclohexanone, acetophenone and propiophenone;

formic acid, acetic acid, propionic acid and butyric acid;

formamide, N,N-dimethyl- and N,N-diethylformamide, N,N-dimethyl- and N,N-diethylacetamide, N,N-dimethyl- and N,N-diethylpropionamide and N-methylpyrrolidone;

dimethyl phthalate and diethyl phthalate;

cyclohexane, benzene, toluene, xylene, mesitylene, ethylbenzene, chlorobenzene, o-dichlorobenzene, trichlorobenzene, naphthalene and methylnaphthalene.

The recrystallization is preferably carried out using solvents which are easy to remove in the workup, for example by washing with water, azeotropic distillation with water, steam distillation or by drying the entire batch (by distilling off the solvent for example).

Particular preference is given to using solvents which have a boiling point $\leq 150°$ C. and can be evaporated without decomposition and without leaving a residue, for example $C_1-C_5$-alkanols, ketones such as methyl ethyl ketone, ethers such as tetrahydrofuran and dioxane and hydrocarbons such as cyclohexane, benzene, toluene, xylene and chlorobenzene and mixtures thereof, of which xylene and toluene are most preferred.

The amount of solvent is generally not critical and can be varied within wide limits. The amount of solvent used per g of millbase is generally in the range from 3 to 6 g, preferably in the range from 4 to 5 g.

The recrystallization is typically carried out at from 25 to 140° C., especially at from 60 to 100° C.

The recrystallization can be effected by dispersing the millbase in the solvent or else by simply allowing the millbase to dwell in the solvent. The mixture of millbase and solvent is preferably stirred.

The duration of the recrystallization step depends on the temperature and the solvent. Generally recrystallization will be complete in the course of from 1 to 10 h.

The finishing process of the invention makes it possible to vary the median particle size of the quinophthalone pigments obtained in a specific manner via the amount of the quinophthalone derivative I and adjust it to whichever value is desired in the range from 50 to 100 nm coupled with a width of ±20 nm for the particle size distribution.

The formation of particularly finely divided quinophthalone pigments is supported on adding further pigment assistants during the finishing process (during the grinding and/or the recrystallization steps).

Particularly useful pigment assistants are additives based on substituted ureas that are obtainable by double addition of amines to aryldiisocyanates. Preference is given to the DE-A-29 06 111 urea derivatives of the formula

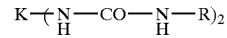

where K is 1,5-naphthylene or 4,4'-diphenylenemethane and R is $C_{12}-C_{18}$-alkyl, $C_{12}-C_{18}$-alkenyl, $C_8-C_{18}$-alkoxypropyl or $-(CH_2)_3-O-(C_2H_4O)_n-O-R^1$, where $R^1$ is $C_2-C_8$-alkyl or phenyl and n is from 1 to 4. An example of a preferred assistant is the product obtained by addition of 2 mol of 3-octoxypropyleneamine onto 1,5-naphthalene diisocyanate.

The pigment preparations obtained in this way preferably include these assistants as component (C) in amounts of from 1 to 10% by weight, based on the quinophthalone pigment (A).

The quinophthalone pigments provided by the finishing process of the invention and correspondingly the similarly inventive pigment preparations including (A) at least one quinophthalone pigment and (B) at least one quinophthalone derivative (B) are notable for excellent color and rheological properties and also fastnesses, especially high transparency, high color strength and high gloss, ease of dispersion and unequivocal overcoating, solvent and weathering fastness. Application in alkyd-melamine baking finishes typically provides the following color properties: hue: 82–86°; lightness $L \geq 80$; chroma $C \geq 90$; transparency, measured in scattering delta E, $\leq 95$ to about 40.

They are very useful for coloring a multiplicity of application media, for example plastics, solventborne and waterborne coatings and, because of their transparency, in particular also printing inks for all common printing processes, for example offset printing, intaglio printing, packaging printing, tinplate printing and textile printing.

More particularly, because they are finely divided, they can also be used in inkjet inks, color filters and electrophotographic toners and developers, for example one-, two- and multi-component powder toners (also known as one- or two-component developers), magnetic toners, liquid toners, polymerization toners and specialty toners (cf. for example U.S. Pat. Nos. 5,607,804 and 5,620,820).

It will be appreciated that they may also be used combined with further colorants, for example with mono- and disazo and isoindoline pigments such as C.I. Pigment Yellow 12, 13, 14, 17, 139 and 185.

EXAMPLES

A) Preparation of Inventive Quinophthalone Derivatives I

Example 1

100 g of C.I. Pigment Yellow 138, prepared according to Example 1 of DE-A-17 70 960, were introduced a little at a time into 500 g of cold 11% by weight oleum at about 10° C. with stirring. The mixture was then heated to 90° C. and stirred at 90° C. for 6 h.

After cooling to 25° C., the reaction mixture was introduced into the 500 g of water. The thusly precipitated product was filtered off, washed sulfate-free with water and dried at 90° C. in a vacuum drying cabinet.

This furnished 108.8 g of the quinophthalone derivative Ia

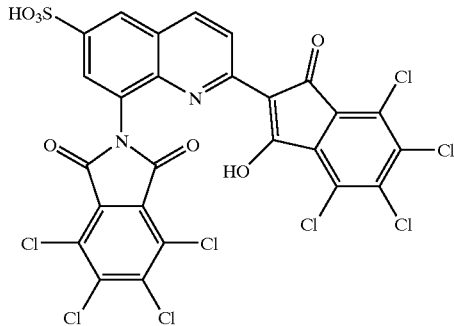

Ia as a dark yellow powder, which corresponds to a yield of 98%.

Analytical Data:

Elemental analysis (% by weight calc./obs.): N, 3.6/3.6; S, 4.1/4.0;

1H NMR (D$_2$SO$_4$): δ=8.1, 8.18, 8.47, 8.61 ppm.

Example 2

A mixture of 200 g of water and 20 g of the quinophthalone derivative Ia of Example 1 were admixed with 43.65 g of a 33% by weight aqueous solution of ditallowdimethylammonium chloride (Arquad® HC, Akzo Chemicals) added dropwise with stirring. The suspension was then heated to 70° C. and stirred at 70° C. for 30 min.

The product obtained was filtered off, washed with water and dried at 90° C. in a vacuum drying cabinet.

This afforded 27.4 g of the ditallowdimethylammonium salt Ib as a yellow powder, which corresponds to a yield of 79%.

Example 3

25.5 g of phthalimide and 7.4 g of paraformaldehyde were alternately introduced with stirring in small portions into 560 g of 3.6% by weight oleum at 25° C. The mixture was then heated to 50° C. and stirred at 50° C. for 30 min. On addition of 100 g of a C. I. Pigment Yellow 138 obtained as described in Example 1, the mixture was heated to 100° C. and stirred at 100° C. for a further 3 h.

The reaction mixture was then introduced into 3500 g of water and the mixture was stirred at 60° C. for 30 min. The thusly precipitated product was filtered off, washed neutral with water and dried at 90° C. in a vacuum drying cabinet.

This furnished 121.2 g of the quinophthalone derivative Ic

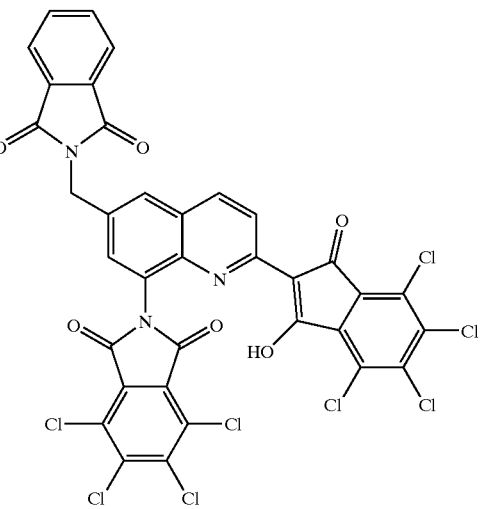

Ic as a golden yellow powder, which corresponds to a yield of 99%.

Analytical Data:

Elemental analysis (% by weight calc./obs.): N, 4.9/4.9; Cl, 33.3/32.4.

Example 4 a) A mixture of 1200 g of chlorosulfonic acid and 200 g of a C. I. Pigment Yellow 138 obtained as described in Example 1 was heated to 120° C. and stirred at 120° C. for 2 h. After cooling to ≦80° C. and subsequent addition of 123 g of thionyl chloride, the mixture was stirred at 80° C. for a further 30 min.

After cooling to 25° C. the reaction mixture was introduced into 3500 g of ice-water together with sufficient further ice for the temperature not to exceed 3° C.

After subsequent stirring for 15 minutes, the precipitated product was filtered off, washed sulfate-free with water and further reacted without drying.

A mixture of 1000 g of ice-water and 614 g of the water-moist product of step a) (strength about 18.5%) was cooled down to <2° C. The pH of the mixture was adjusted to 8.7 with about 8 g of sodium carbonate. It was then admixed with a mixture (adjusted to pH 7 with 8.15 g of glacial acetic acid) of 29 g of tridecylamine and 100 g of water added dropwise over 30 min with stirring. The pH, which dropped to 5.7, was adjusted to 7 with sodium carbonate.

After subsequent stirring for one hour, the product was filtered off, washed neutral with water and dried at 90° C. in a vacuum drying cabinet.

This furnished 131 g of the quinophthalone derivative Id

Id $H_{27}C_{13}NHO_2S$

[chemical structure of Id]

as a yellow powder, which corresponds to a yield of 95%.

Analytical Data:

Elemental analysis (% by weight calc./obs.): C, 49.0/49.5; N, 4.4/4.4; Cl, 29.7/30.4.

B) Preparation and Use of Inventive Pigment Preparations

Examples 5 to 26

Variant A 100 g of C.I. Pigment Yellow 138 in the form of the crude pigment obtained according to Example 1 of DE-A-17 70 960 were milled with about 1900 g of iron balls 2 cm in diameter in a 1 l capacity vibratory mill for 40 h.

A mixture of 97 g of the millbase, x g of the quinophthalone derivative I, y g of the amine A and 300 g of xylene was then stirred at 65° C. for 5 h. The solvent was subsequently distilled off under reduced pressure at 120° C., and the product was dried down to a xylene content <0.1%.

Variant B

Grinding was carried out similarly to variant A, except that 97 g of the crude pigment were ground in the presence of x g of the quinophthalone derivative I.

The millbase obtained was recrystallized similarly to variant A in xylene in the presence of y g of amine A.

In both variants, the finished pigment was subsequently pulverized and tested.

In all cases, the finished C.I. Pigment Yellow 138 obtained was observed under the electron microscope to have a $d_{50}$ particle size e range from 50 to 100 nm coupled with a width of ±20 nm for the particle size distribution.

The pigment obtained in each case was very easy to disperse in all application media. Incorporation into an alkyd-melamine baking finish provided a transparent and brilliant yellow hue having a very greenish tinge.

Details concerning these experiments are reported in Table 1.

Keys to the Designations Used:

Amine A1: ditallowdimethylammonium chloride (Arquad HC, Akzo Chemicals)

Amine A2: ditallowmethylamine (Armeen® M2HT, Akzo Chemicals)

Amine A3: dehydroabietylamine (Amine D, Hercules)

TABLE 1

| Ex. | Variant | x g | Quinophthalone derivative I | y g | Amine A |
|---|---|---|---|---|---|
| 5 | A | 1,5 | Ia | — | — |
| 6 | B | 1.5 | Ia | — | — |
| 7 | A | 3 | Ia | — | — |

TABLE 1-continued

| Ex. | Variant | x g | Quinophthalone derivative I | y g | Amine A |
|---|---|---|---|---|---|
| 8 | B | 3 | Ia | — | — |
| 9 | A | 3 | Ib | — | — |
| 10 | B | 3 | Ib | — | — |
| 11 | A | 3 | Ic | — | — |
| 12 | B | 3 | Ic | — | — |
| 13 | A | 3 | Id | — | — |
| 14 | B | 3 | Id | — | — |
| 15 | A | 1.8 | Ia | 1.2 | A1 |
| 16 | B | 1.8 | Ia | 1.2 | A1 |
| 17 | A | 1.8 | Ia | 1.2 | A2 |
| 18 | B | 1.8 | Ia | 1.2 | A2 |
| 19 | A | 1.8 | Ia | 1.2 | A3 |
| 20 | B | 1.8 | Ia | 1.2 | A3 |
| 21 | A | 3 | Ia | 3 | A1 |
| 22 | B | 3 | Ia | 3 | A1 |
| 23 | A | 3 | Ia | 3 | A2 |
| 24 | B | 3 | Ia | 3 | A2 |
| 25 | A | 3 | Ia | 3 | A3 |
| 26 | B | 3 | Ia | 3 | A3 |

C) Preparation of Inkjet Inks

Example 27

15 g of the pigment preparation of Example 5, 10 g of a dispersant D based on an oxalkylated phenol (described as dispersant 13 in U.S. Pat. No. 4,218,218), 5 g of 1,2-propylene glycol and 0.5 g of a 10% by weight solution of 1,2-benzisothiazolin-3-one in aqueous propylene glycol (biocide E1) were bulked with completely ion-free water to a total weight of 100 g and pasted up in a mill.

For final adjustment (4% by weight preparation) 26.7 g of the mixture obtained were admixed with 3 g of triethylene glycol monobutyl ether, 5 g of polyethylene glycol ($M_w$ 400 g/mol), 6 g of polytetrahydrofuran 250 ($M_w$ 250 g/mol, BASF), 6 g of glycerol, a further 0.4 g of biocide E1, 0.5 g of a wetting agent F based on an initially ethoxylated and then propoxylated 2-(3-hydroxypropyl) heptamethyltrisiloxane (11 mol EO/5 mol PO) and 1 g of urea, bulked with water to a total weight of 100 g, mixed and filtered through a sieve having a pore size of 1 µm.

Examples 28 and 29

The inkjet inks of Examples 28 and 29 were prepared similarly to Example 27.

Further particulars of the inkjet inks obtained are reported in Table 2. Percentages are by weight. Biocide E2 is a 20% by weight solution of 1,2-benzisothiazolin-3-one in aqueous ethylene glycol.

TABLE 2

| | Inkjet ink | | |
|---|---|---|---|
| | Ex. 27 | Ex. 28 | Ex. 29 |
| Pigment prep. Ex. 5 | 4% | 2% | 4.5% |
| Dispersant D | 2.7% | 1.3% | 3% |
| Polytetrahydrofuran 250 | 6% | 6% | 6% |
| Glycerol | 6% | 6% | 6% |
| 1,2-Propylene glycol | 1.4% | 0.7% | 1.5% |
| Triethylene glycol monobutyl ether | 3% | 5% | 5% |
| Polyethylene glycol 400 | 5% | 4% | 4% |
| Urea | 1% | 1% | 1% |
| Wetting agent F | 0.5% | 0.5% | — |
| Biocide E1 | 0.4% | 0.07% | 0.15% |

TABLE 2-continued

| | Inkjet ink | | |
|---|---|---|---|
| | Ex. 27 | Ex. 28 | Ex. 29 |
| Biocide E2 | — | 0.4% | 0.4% |
| Completely ion-free water | 70% | 75.03% | 70.45% |
| Total | 100% | 100% | 100% |

We claim:

1. A quinophthalone compound represented by formula I:

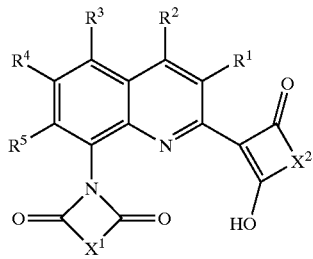

wherein

R$^1$, R$^2$, R$^3$ and R$^5$ are independently hydrogen, halogen or C$_1$–C$_4$—alkyl;

R$^4$ is —SO$_3$H, —SO$_3^-$N$^+$R$^6$R$^7$R$^8$R$^9$, —SO$_2$NR$^6$R$^7$, —CH$_2$NR$^6$R$^7$, —CH$_2$R$^{10}$, —COOH, —COO$^-$N$^+$R$^6$R$^7$R$^8$R$^9$, —COOR$^{11}$, —COR$^{11}$, —NO$_2$ or C$_1$–C$_4$—alkyl;

R$^6$, R$^7$, R$^8$ and R$^9$ are independently hydrogen; C$_1$–C$_{22}$—alkyl or C$_2$–C$_{22}$-alkenyl whose carbon chains may be interrupted by one or more moieties selected from the group consisting of —O—, —S—, —NR$^{12}$—, —CO— and —SO$_2$— and/or which may each be mono- or polysubstituted by hydroxyl, halogen, aryl, C$_1$–C$_4$-alkoxy and/or acetyl; C$_3$–C$_8$—cycloalkyl whose carbon skeleton may be interrupted by one or more moieties selected from the group consisting of —O—, —S—, —NR$^{12}$— and —CO— and/or which may be mono- or polysubstituted by hydroxyl, halogen, aryl, C$_1$–C$_4$—alkoxy and/or acetyl; dehydroabietyl or aryl; R$^6$ and R$^7$ or R$^6$, R$^7$ and R$^8$ are together a 5- to 7-membered cyclic radical which includes the nitrogen atom and may include further heteroatoms;

R$^{10}$ is

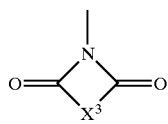

R$^{11}$ is alkyl R$^6$;

R$^{12}$ is hydrogen or C$_1$–C$_4$—alkyl;

X$^1$, X$^2$ and X$^3$ are independently arylene, which may be substituted by halogen, arylsulfonyl or —COR$^{13}$ or —CO—C$_6$H$_4$—CO—;

R$^{13}$ is C$_1$–C$_3$-alkyl or phenyl.

2. The quinophthalone compound of claim 1, wherein R$^1$, R$^2$, R$^3$ and R$^5$ are each hydrogen;

R$^4$ is —SO$_3$H, —SO$_3^-$N$^+$R$^6$R$^7$R$^8$R$^9$, —SO$_2$NR$^6$R$^7$, —CH$_2$NR$^6$R$^7$ or —CH$_2$R$^{10}$;

R$^6$, R$^7$, R$^8$ and R$^9$ are independently hydrogen; C$_1$–C$_{22}$—alkyl or C$_2$–C$_{22}$—alkenyl whose carbon chains may be interrupted by one or more moieties selected from the group consisting of —O—, —S—, NR$^{12}$—, —CO— and —SO$_2$— and which may each be mono- or polysubstituted by hydroxyl, halogen, aryl, C$_1$–C$_4$—alkoxy and/or acetyl; cyclohexyl; dehydroabietyl or aryl;

R$^{10}$ is

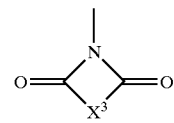

R$^{12}$ is hydrogen or C$_1$–C$_4$—alkyl;

X$^1$ and X$^2$ are each 1,2—phenylene, which may bear up to 4 halogen atoms as substituents;

X$^3$ is arylene, which may be substituted by halogen, arylsulfonyl or —COR$^{13}$ or —CO—C$_6$H$_4$—CO—;

R$^{13}$ is C$_1$–C$_3$—alkyl or phenyl.

3. The quinophthalone compound of claim 1, wherein R$^4$ is —SO$_3$H, —SO$_3^-$N$^+$R$^6$R$^7$R$^8$R$^9$, —SO$_2$NR$^6$R$^7$, —CH$_2$NR$^6$R$^7$, —CH$_2$R$^{10}$, —COOH, —COO$^-$NR$^+$R$^6$R$^7$R$^8$R$^9$, —COOR$^{11}$, —COR$^{11}$, or —NO$_2$.

4. The quinophthalone compound of claim 1, wherein R$^4$ is —SO$_3$H, —SO$_3^-$N$^+$R$^6$R$^7$R$^8$R$^9$, —SO$_2$NR$^6$R$^7$, —CH$_2$NR$^6$R$^7$, —CH$_2$R$^{10}$, —COOH, —COO$^-$N$^+$R$^6$R$^7$R$^8$R$^9$, —COOR$^{11}$, or —COR$^{11}$.

5. A method of modifying an organic pigment, comprising crystallizing an organic pigment in the presence of one or more quinophthalone compounds represented by formula I:

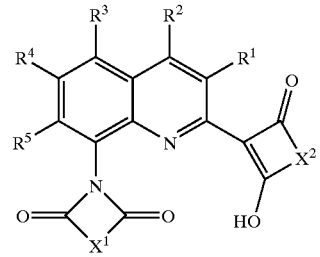

wherein

R$^1$, R$^2$, R$^3$ and R$^5$ are independently hydrogen, halogen or C$_1$–C$_4$-alkyl;

R$^4$ is —SO$_3$H, —SO$_3^-$N$^+$R$^6$R$^7$R$^8$R$^9$, —SO$_2$NR$^6$R$^7$, —CH$_2$NR$^6$R$^7$, —CH$_2$R$^{10}$, —COOH, —COO$^-$N$^+$R$^6$R$^7$R$^8$R$^9$, —COOR$^{11}$, —COR$^{11}$, —NO$_2$ or C$_1$–C$_4$—alkyl;

R$^6$, R$^7$, R$^8$ and R$^9$ are independently hydrogen; C$_1$–C$_{22}$—alkyl or C$_2$–C$_{22}$—alkenyl whose carbon chains may be interrupted by one or more moieties selected from the group consisting of —O—, —S—, —NR$^{12}$—, —CO— and —SO$_2$— and/or which may each be mono- or polysubstituted by hydroxyl, halogen, aryl, C$_1$–C$_4$-alkoxy and/or acetyl; C$_3$–C$_8$-cycloalkyl whose carbon skeleton may be interrupted by one or more moieties selected from the group consisting of —O—, —S—, —NR$^{12}$— and —CO— and/or which may be mono- or polysubstituted by hydroxyl, halogen, aryl, C$_1$–C$_4$-alkoxy and/or acetyl; dehydroabietyl or aryl; R$^6$ and R$^7$ or R$^6$, R$^7$ and R$^8$ are together a 5- to 7-membered cyclic radical which includes the nitrogen atom and may include further heteroatoms;

$R^{10}$ is

[structure: 4-membered ring with N at top (bearing bond up), two C=O groups flanking, and $X^3$ at bottom]

$R^{11}$ is alkyl $R^6$;

$R^{12}$ is hydrogen or $C_1$–$C_4$—alkyl;

$X^1$, $X^2$ and $X^3$ are independently arylene, which may be substituted by halogen, arylsulfonyl or —$COR^{13}$ or —CO—$C_6H_4$—CO—; and $R^{13}$ is $C_1$–$C_3$—alkyl or phenyl.

6. The method of claim 5, wherein $R^1$, $R^2$, $R^3$ and $R^5$ are each hydrogen;

$R^4$ is —$SO_3H$, —$SO_3^-N^+R^6R^7R^8R^9$, —$SO_2NR^6R^7$, —$CH_2NR^6R^7$ or —$CH_2R^{10}$ $R^6$, $R^7$, $R^8$ and $R^9$ are independently hydrogen; $C_1$–$C_{22}$—alkyl or $C_2$–$C_{22}$-alkenyl whose carbon chains may be interrupted by one or more moieties selected from the group consisting of —O—, —S—, —$NR^{12}$—, —CO— and —$SO_2$— and which may each be mono- or polysubstituted by hydroxyl, halogen, aryl, $C_1$–$C_4$-alkoxy and/or acetyl; cyclohexyl; dehydroabietyl or aryl;

$R^{10}$ is

[structure: 4-membered ring with N at top, two C=O, and $X^3$ at bottom]

$R^{12}$ is hydrogen or $C_1$–$C_4$—alkyl;

$X^1$ and $X^2$ are each 1,2-phenylene, which may bear up to 4 halogen atoms as substituents;

$X^3$ is arylene, which may be substituted by halogen, arylsulfonyl or —$COR^{13}$ or —CO—$C_6H_4$—CO—;

$R^{13}$ is $C_1$–$C_3$—alkyl or phenyl.

7. The method of claim 5, wherein $R^4$ is —$SO_3H$, —$SO_3^-N^+R^6R^7R^8$, $R^9$, —$SO_2NR^6R^7$, —$CH_2NR^6R^7$, —$CH_2R^{10}$, —COOH, —COO$^-N^+R^6R^7R^8R^9$, —$COOR^{11}$, —$COR^{11}$, or —$NO_2$.

8. The method of claim 5, wherein $R^4$ is —$SO_3H$, —$SO_3^-N^+R^6R^7R^8R^9$, —$SO_2NR^6R^7$, —$CH_2NR^6R^7$, —$CH_2R^{10}$, —COOH, —COO$^-N^+R^6R^7R^8R^9$, —$COOR^{11}$, or —$COR^{11}$.

9. A process for transforming crude quinophthalone pigments into a finely divided pigmentary state, comprising:

grinding a crude quinophthalone pigment in the absence of grinding assistants to obtain a millbase; and recrystalizing the millbase in an organic solvent or a mixture of organic solvent and water in the presence of one or more quinophthalone compounds represented by formula I:

[structure: quinoline ring system with substituents $R^1$, $R^2$, $R^3$, $R^4$, $R^5$ on the benzo ring, N-substituted with a 4-membered ring containing $X^1$ and two C=O (attached at position 8), and at position 2 attached to a cyclobutenedione-like ring with $X^2$ and HO substituent]   I wherein $R^1$, $R^2$, $R^3$ and $R^5$ are independently hydrogen, halogen or $C_1$–$C_4$-alkyl;

$R^4$ is —$SO_3H$, —$SO_3^-N^+R^6R^7R^8R^9$, —$SO_2NR^6R^7$, —$CH_2NR^6R^7$, —$CH_2R^{10}$, —COOH, —COO$^-N^+R^6R^7R^8R^9$, —$COOR^{11}$, —$COR^{11}$, —$NO_2$ or $C_1$–$C_4$-alkyl;

$R^6$, $R^7$, $R^8$ and $R^9$ are independently hydrogen; $C_1$–$C_{22}$—alkyl or $C_2$–$C_{22}$—alkenyl whose carbon chains may be interrupted by one or more moieties selected from the group consisting of —O—, —S—, —$NR^{12}$—, —CO— and —$SO_2$— and/or which may each be mono- or polysubstituted by hydroxyl, halogen, aryl, $C_1$–$C_4$-alkoxy and/or acetyl; $C_3$–$C_8$-cycloalkyl whose carbon skeleton may be interrupted by one or more moieties selected from the group consisting of —O—, —S—, —$NR^{12}$— and —CO— and/or which may be mono- or polysubstituted by hydroxyl, halogen, aryl, $C_1$–$C_4$-alkoxy and/or acetyl; dehydroabietyl or aryl; $R^6$ and $R^7$ or $R^6$, $R^7$ and $R^8$ are together a 5- to 7-membered cyclic radical which includes the nitrogen atom and may include further heteroatoms;

$R^{10}$ is

[structure: 4-membered ring with N at top, two C=O, and $X^3$ at bottom]

$R^{11}$ is alkyl $R^6$;

$R^{12}$ is hydrogen or $C_1$–$C_4$—alkyl;

$X^1$, $X^2$ and $X^3$ are independently arylene, which may be substituted by halogen, arylsulfonyl or —$COR^{13}$ or —CO—$C_6H_4$—CO—; and $R^{13}$ is $C_1$–$C_3$—alkyl or phenyl.

10. The process of claim 9, wherein $R^1$, $R^2$, $R^3$ and $R^5$ are each hydrogen;

$R^4$ is —$SO_3H$, —$SO_3^-N^+R^6R^7R^8R^9$, —$SO_2NR^6R^7$, —$CH_2NR^6R^7$ or —$CH_2R^{10}$ $R^6$, $R^7$, $R^8$ and $R^9$ are independently hydrogen; $C_1$–$C_{22}$—alkyl or $C_2$–$C_{22}$-alkenyl whose carbon chains may be interrupted by one or more moieties selected from the group consisting of —O—, —S—, —$NR^{12}$—, —CO— and —$SO_2$— and which may each be mono- or polysubstituted by hydroxyl, halogen, aryl, $C_1$–$C_4$—alkoxy and/or acetyl; cyclohexyl; dehydroabietyl or aryl;

$R^{10}$ is

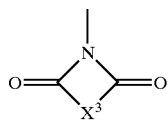

$R^{12}$ is hydrogen or $C_1$–$C_4$—alkyl;

$X^1$ and $X^2$ are each 1,2—phenylene, which may bear up to 4 halogen atoms as substituents;

$X^3$ is arylene, which may be substituted by halogen, arylsulfonyl or —COR$^{13}$ or —CO—$C_6H_4$—CO—;

$R^{13}$ is $C_1$–$C_3$—alkyl or phenyl.

11. The method of claim 9, wherein $R^4$ is —SO$_3$H, —SO$_3$N$^+$R$^6$R$^7$R$^8$R$^9$, —SO$_2$NR$^6$R$^7$, —CH$_2$NR$^6$R$^7$, —CH$_2$R$^{10}$, —COOH, —COO$^-$N$^+$R$^6$R$^7$R$^8$R$^9$, —COOR$^{11}$, —COR$^{11}$, or —NO$_2$.

12. The method of claim 9, wherein $R^4$ is —SO$_3$H, —SO$_3^-$N$^+$R$^6$R$^7$R$^8$R$^9$, —SO$_2$NR$^6$R$^7$, —CH$_2$NR$^6$R$^7$, —CH$_2$R$^{10}$, —COOH, —COO$^-$N$^+$R$^6$R$^7$R$^8$R$^9$, —COOR$^{11}$, or —COR$^{11}$.

13. The process of claim 9, wherein the crude quinophthalone pigment is ground in the presence of the quinophthalone derivative and the millbase is subsequently recrystallized in an organic solvent or a mixture of organic solvent and water.

14. A quinophthalone pigment represented by formula II:

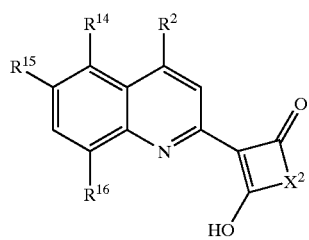

II wherein $R^2$ is hydrogen, halogen or $C_1$–$C_4$—alkyl;

one of $R^{14}$, $R^{15}$ and $R^{16}$ is

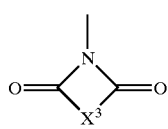

and the others are each hydrogen;

$X^1$ and $X^2$ are independently arylene, which may be substituted by halogen, arylsulfonyl or —COR$^{12}$ or —CO—$C_6H_4$—CO—;

$R^{12}$ is $C_1$–$C_3$-alkyl or phenyl, having an isometric particle shape and particle size of from 50 to 200 nm coupled with a width of ±20 nm for the particle size distribution.

15. A pigment preparation, comprising:
A) at least one quinophthalone pigment of formula II as set forth in claim 14 and
B) at least one quinophthalone derivative of the formula I

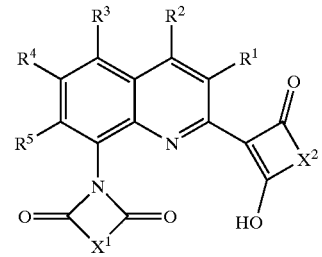

I wherein $R^1$, $R^2$, $R^3$ and $R^5$ are independently hydrogen, halogen or $C_1$–$C_4$—alkyl;

$R^4$ is —SO$_3$H, —SO$_3$—N$^+$R$^6$R$^7$R$^8$R$^9$, —SO$_2$NR$^6$R$^7$, —CH$_2$NR$^6$R$^7$, —CH$_2$R$^{10}$, —COOH, —COO$^-$N$^+$R$_6$R$_7$R$_8$R$_9$, —COOR$^{11}$, —COR$^{11}$, —NO$_2$ or $C_1$–$C_4$—alkyl;

$R^6$, $R^7$, $R^8$ and $R^9$ are independent hydrogen; $C_1$–$C_{22}$—alkyl or $C_2$–$C_{22}$—alkenyl whose carbon chains may be interrupted by one or more moieties selected from the group consisting of —O—, —S—, —NR$^{12}$—, —CO— and SO$^2$— and/or which may each be mono- or polysubstituted by hydroxyl, halogen, aryl, $C_1$–$C_4$—alkoxy and/or acetyl; $C_3$–$C_8$—cycloalkyl whose carbon skeleton may be interrupted by one or more moieties selected from the group consisting of —O—, —S—, —NR$^{12}$— and —CO— and/or which may be mono- or polysubstituted by hydroxyl, halogen, aryl, $C_1$–$C_4$—alkoxy and/or acetyl; dehydroabietyl or aryl; $R^6$ and $R^7$ or $R^6$, $R^7$ and $R^8$ are together a 5- to 7-membered cyclic radical which includes the nitrogen atom and may include further heteroatoms;

$R^{10}$ is

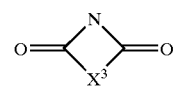

$R^{11}$ is alkyl $R^6$;

$R^{12}$ is hydrogen or $C_1$–$C_4$—alkyl;

$X^1$, $X^2$ and $X^3$ are independently arylene, which may be substituted by halogen, arylsulfonyl or —COR$^{13}$ or —CO—$C_6H_4$—CO—; and $R^{13}$ is $C_1$–$C_3$—alkyl or phenyl.

16. The pigment preparation of claim 15, which contains from 1 to 10% by weight of the quinophthalone derivative (B), based on the quinophthalone pigment (A).

17. A method of coloring coloring plastics, paints, printing inks, inkjet inks, color filters, electrophotographic toners and electrophotographic developers, comprising incorporating an effective amount of the pigment preparation of claim 15 into a plastic, paint, printing ink, inkjet ink, color filter, electrophotographic toners or electrophotographic developer.

18. A method of coloring coloring plastics, paints, printing inks, inkjet inks, color filters, electrophotographic toners and electrophotographic developers, comprising incorporating an effective amount of the pigment preparation of claim 16 into a plastic, paint, printing ink, inkjet ink, color filter, electrophotographic toners or electrophotographic developer.

* * * * *